(12) United States Patent
Shack

(10) Patent No.: US 10,060,156 B1
(45) Date of Patent: Aug. 28, 2018

(54) SANITIZER DOOR KNOB SYSTEMS

(71) Applicant: Christopher Shack, Melbourne, FL (US)

(72) Inventor: Christopher Shack, Melbourne, FL (US)

( * ) Notice: Subject to any disclaimer, the term of this patent is extended or adjusted under 35 U.S.C. 154(b) by 45 days.

(21) Appl. No.: 14/527,173

(22) Filed: Oct. 29, 2014

Related U.S. Application Data

(60) Provisional application No. 61/947,985, filed on Mar. 4, 2014.

(51) Int. Cl.
*A61L 2/22* (2006.01)
*E05B 1/00* (2006.01)

(52) U.S. Cl.
CPC ............... *E05B 1/0069* (2013.01); *A61L 2/22* (2013.01)

(58) Field of Classification Search
CPC .................. E05B 1/0069; A61L 2/22
See application file for complete search history.

(56) References Cited

U.S. PATENT DOCUMENTS

| | | |
|---|---|---|
| 3,314,746 A | 4/1967 | Millar |
| 6,645,435 B2 | 11/2003 | Dawson et al. |
| 6,874,697 B2 | 4/2005 | Callueng |
| 2004/0223894 A1* | 11/2004 | Gilbert ...................... A61L 2/18 422/292 |

\* cited by examiner

*Primary Examiner* — Donald R Spamer
(74) *Attorney, Agent, or Firm* — RG Patent Consulting, LLC; Rachel Gilboy

(57) ABSTRACT

The sanitizer door knob system has a door knob assembly that emits sanitizing liquid when turned in either direction. In a set, only one knob will emit the sanitizer fluid. The inside of the knob that does emit the liquid has a pull rod that pulls an internal pump upon the turning of the knob and cause the sanitizing liquid to be projected from its reservoir tube. A slider cap on the exterior of the knob opens to allow the sanitizer to be emitted. Door knob assembly may comprise a recoil spring on both the first and second door knob.

20 Claims, 5 Drawing Sheets

SANITIZER DOOR KNOB SYSTEMS

CROSS-REFERENCE TO RELATED APPLICATION

The present application is related to and claims priority from prior provisional application Ser. No. 61/947,985, filed Mar. 4, 2014 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of doors and door knobs and more specifically relates to a sanitizer door knob system.

2. Description of the Related Art

Many individuals in modern society live and/or work within residential and commercial buildings. Typically, these buildings have doors to allow ingress and egress of the structures and the rooms located within the building. The doors are used by a variety of individuals who often contact the door with their hands to manipulate the door between open and closed positions. Bacteria and other microorganisms which may be found on the hands of the individual(s) are the cause of many diseases and are easily transmitted from infected individuals to other persons if sanitary conditions are not maintained on these doors, when touched. Restrooms are rooms within these buildings where bacteria, viruses and other disease-producing substances may be found. It is commonplace to find disease causing organisms on a variety of surfaces in bathrooms which may be spread throughout the building via hand transmission.

Individuals using bathrooms can protect themselves from these organisms by thorough washing and drying of their hands; however many do not wash and thus compromise public health when contacting door knobs as they leave the facilities. Microbiological activity may be minimized on the surfaces of door handles by spraying or wiping them with strong disinfectant. This is inconvenient to do on a continuous basis; an automatic means for providing this function is desirable in the interest of public health.

Various attempts have been made to solve the above-mentioned problems such as those found in U.S. Pat. No. 6,874,697 to Ronel Domingo Callueng, U.S. Pat. No. 6,645,435 to Paul Wesley Dawson et al, and U.S. Pat. No. 3,314,746 to Rutherford Y Millar. This art is representative of functional door knobs. None of the above inventions and patents, taken either singly or in combination, is seen to describe the invention as claimed.

Ideally, a sanitizer door knob system should provide public health protection for its users and, yet would operate reliably and be manufactured at a modest expense. Thus, a need exists for a reliable sanitizer door knob system to avoid the above-mentioned problems.

BRIEF SUMMARY OF THE INVENTION

In view of the foregoing disadvantages inherent in the known door knob art, the present invention provides a novel sanitizer door knob system. The general purpose of the present invention, which will be described subsequently in greater detail is to provide a means of public health protection.

A sanitizer door knob system is disclosed herein, in a preferred embodiment, comprising: a door knob assembly (having a first knob, a second knob opposing the first knob, at least one connector shaft, and a latch assembly), a sanitizer dispensing assembly (including a pull rod, a gear box preferably with a pulley, at least one spring), a dispensing tube (having a first-end, a second-end, and a dispensing-tube-length), a dispensing-tube-shroud, and a pump, and further comprising a reservoir structured and arranged to be mounted in (or to) a door. The door in these embodiments comprises an inlet by which a user can access and fill the reservoir located inside the door, wherein the reservoir comprises a corrosion-resistant housing.

The sanitizer door knob system comprises the door knob assembly, the sanitizer dispensing assembly, and the reservoir in functional combination, wherein the door knob assembly comprises the first knob, the second knob, the at least one connector shaft, and the a latch assembly, the first knob and the second knob connected via the at least one connector shaft; the at least one connector shaft preferably passes perpendicularly through the latch assembly. The sanitizer dispensing assembly comprises in functional combination the pull rod, the gear box, the at least one spring, the dispensing tube, the dispensing-tube-shroud and the pump; wherein the gear box comprises a set of meshed gears and a pulley. In preferred embodiments a terminal end of the pull rod may be wrapped and affixed about (and to) the pulley such that movement of the pulley in a clockwise and counterclockwise direction pulls on the pull rod to create the desired action (activation of the manual pump). The pull rod is preferably a flexible cable.

The dispensing tube comprises the first-end, the second-end, and the dispensing-tube-length; the dispensing-tube-length of the dispensing tube defined by the first-end, and the second-end, wherein the dispensing tube is in fluid communication with the reservoir. The reservoir stores fluid comprising sanitizing liquid to be dispensed via the pump through the second-end of the dispensing tube, the first-end of the dispensing tube connected to the reservoir. The pump is activated via relative turning movement of the first knob and the second knob; the gear box being rotationally operated via the at least one connector shaft as moved by turning of the first knob and the second knob. The dispensing tube travels through the dispensing-tube-shroud; the dispensing tube protected along its length via the dispensing-tube-shroud. The second-end of the dispensing tube comprises a nozzle (with small apertures) which is adjacent the second knob such that the sanitizing liquid is able to be 'atomized' by the pump and pushed through the nozzle; the sanitizing liquid able to be dispensed onto the second knob to prevent transfer of microorganisms (bacteria, viruses, and the like).

The pump is caused to 'pump' the sanitizing liquid as it is pulled into a pumping condition by the pull rod via the movement of the gear box and returned to a non-pumping condition by the at least one spring (the pump is thus manually operated in this manner in preferred embodiments; electrically activated pumps may be used in alternate embodiments and equipping of such alternate embodiments is understood to be known to those knowledgeable in the art); wherein the pump is activated by a clockwise relative movement and alternately a counter-clockwise relative movement of the second knob. As such the sanitizer door knob system functions to promote public health by preventing transfer of the microorganisms from off of the door knob assembly via dispensing of the sanitizing liquid thereon.

A kit is also described herein including: the door knob assembly, the sanitizer dispensing assembly, the reservoir, and a set of user-instructions.

A method of using a sanitizer door knob system is disclosed herein comprising the steps of: installing a sanitizer door knob system, filling a reservoir with sanitizing liquid, and opening and closing a door via a door knob assembly equipped with a sanitizer dispensing assembly causing a sanitizing liquid to be dispensed onto at least a portion of the contacted door knob assembly. The method may further comprise the step of refilling the sanitizing liquid into the reservoir as necessary.

The present invention holds significant improvements and serves as a sanitizer door knob system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, sanitizer door knob system, constructed and operative according to the teachings of the present invention.

The various embodiments of the present invention will hereinafter be described in conjunction with the appended drawings, wherein like designations denote like elements.

DETAILED DESCRIPTION

Figure 1:
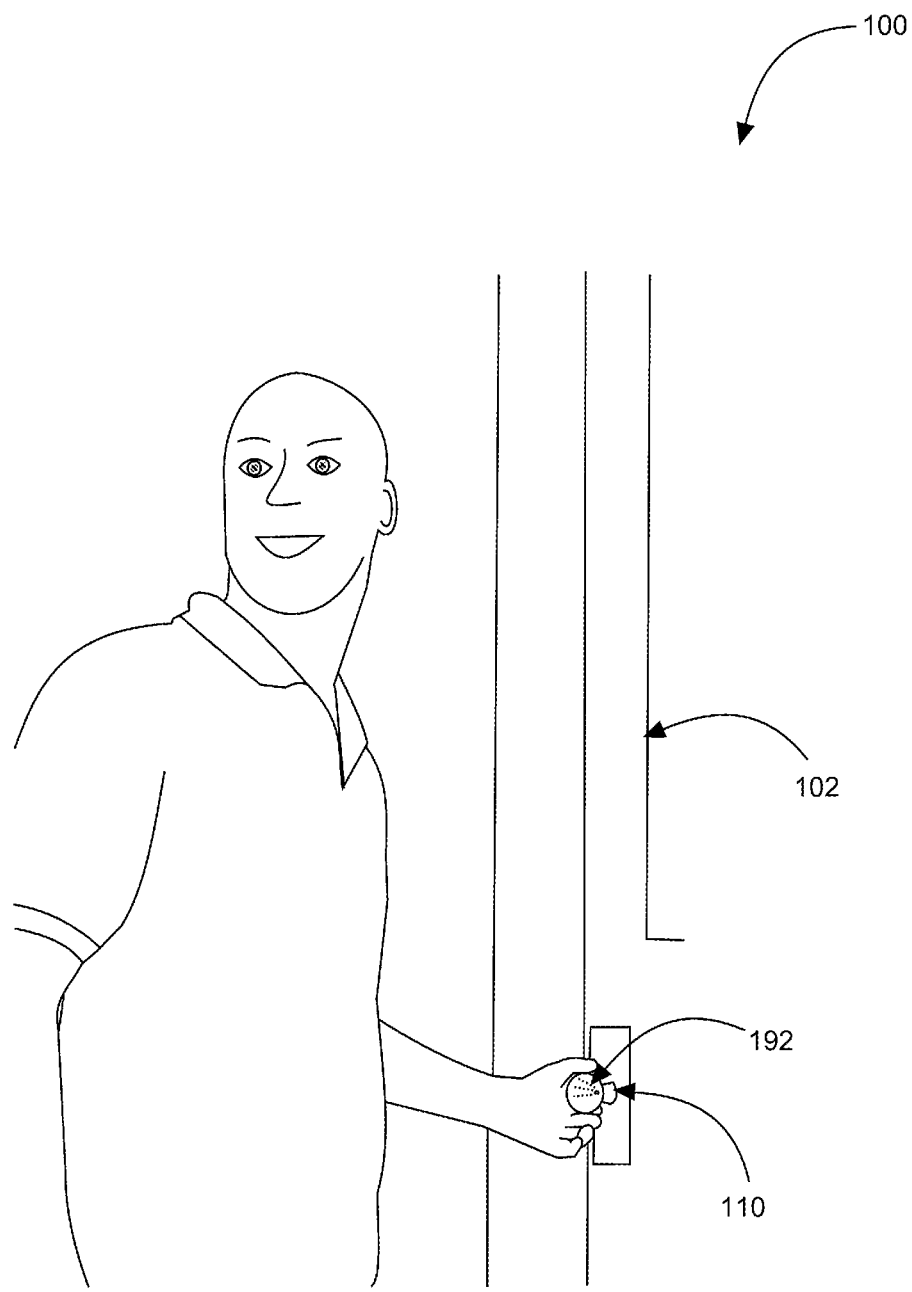
FIG. 1 shows a perspective view illustrating a sanitizer door knob system in an in-use condition according to an embodiment of the present invention.
Figure 2:
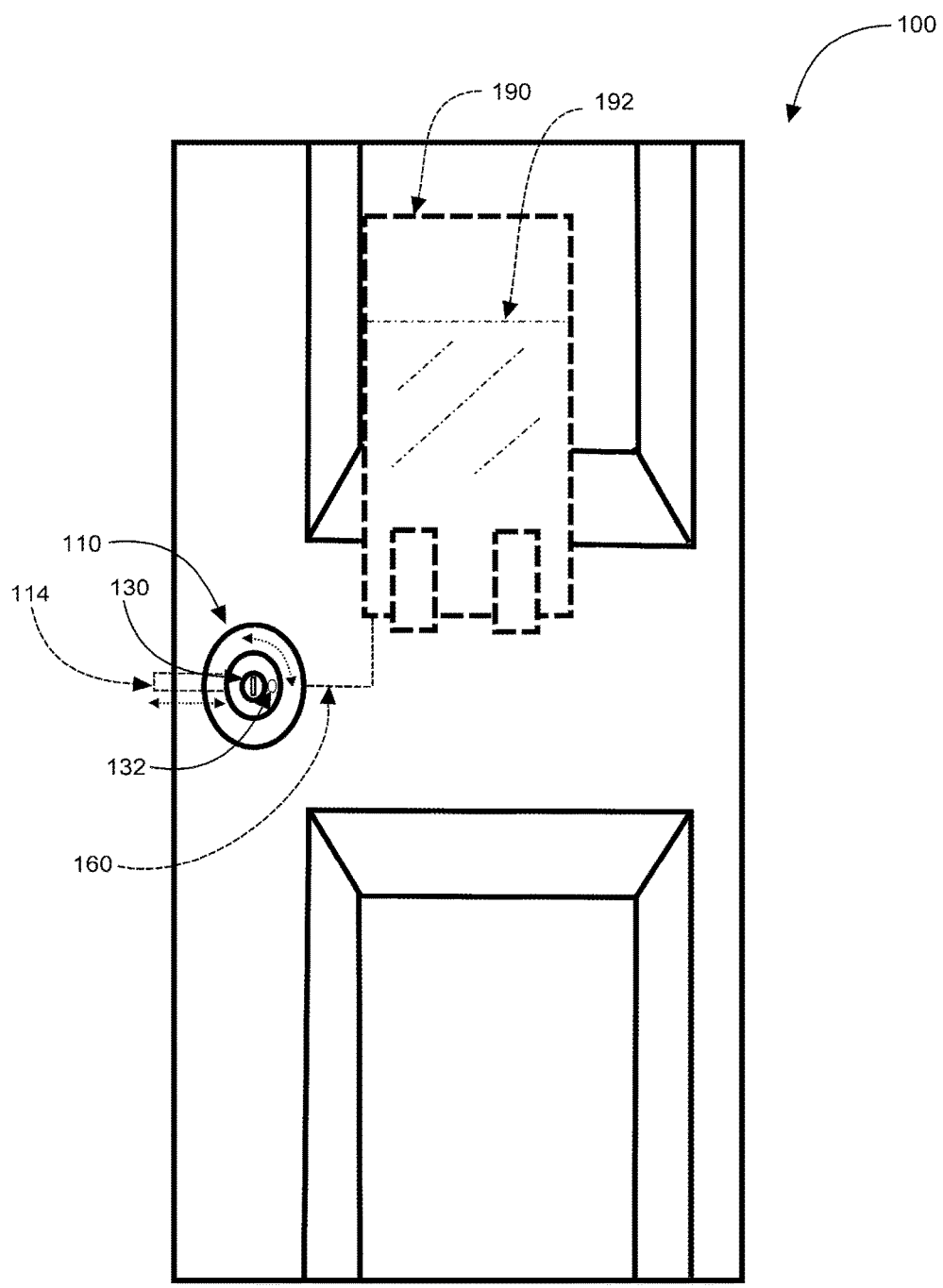
FIG. 2 is a perspective view illustrating a sanitizer door knob assembly of the sanitizer door knob system according to an embodiment of the present invention of FIG. 1.
Figure 3:
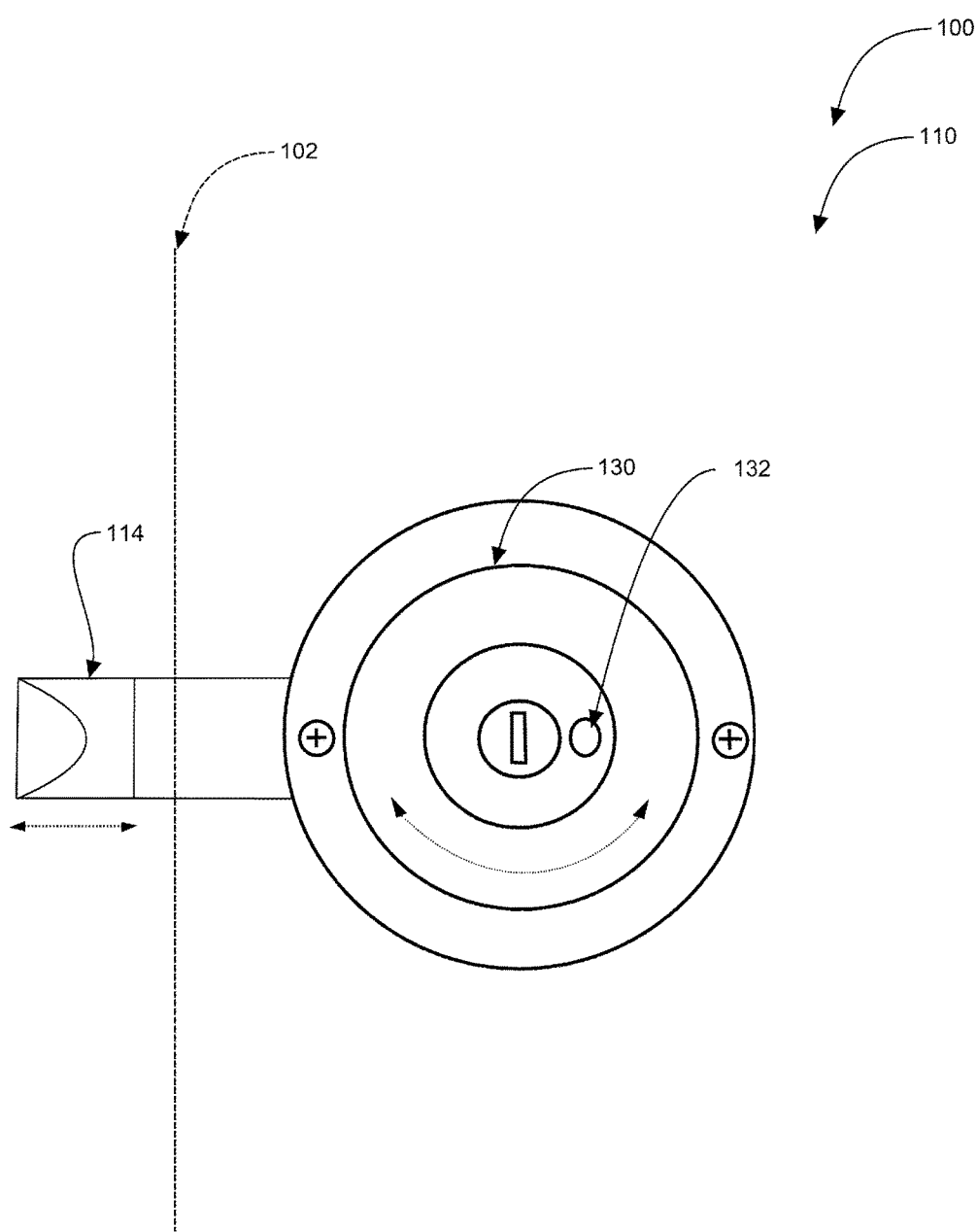
FIG. 3 is another perspective view illustrating the sanitizer door knob assembly according to an embodiment of the present invention of FIG. 1.
Figure 4:
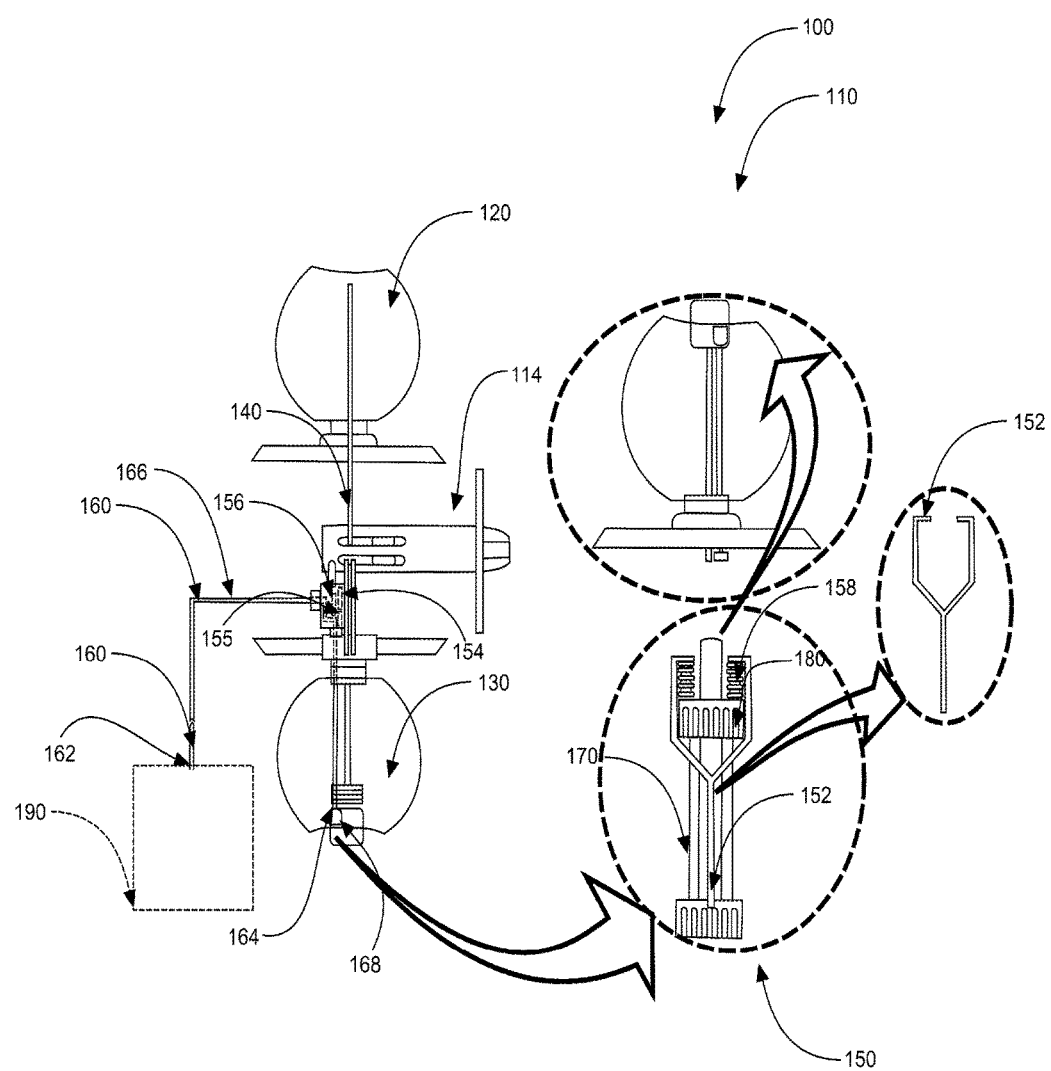
FIG. 4 is yet another perspective view illustrating the sanitizer door knob assembly according to an embodiment of the present invention of FIG. 1.

As discussed above, embodiments of the present invention relate to a door knob and more particularly to a sanitizer door knob system as used to improve the public health.

Generally speaking, the sanitizer door knob is a door knob that will emit sanitizing liquid when turned to either side. In a set, only one knob will emit the sanitizer fluid. The inside of the knob that does emit the liquid will have a pull rod that will pull an internal pump upon the turning of the knob and cause the sanitizing liquid to be projected from its reservoir tube. A slider cap on the exterior of the knob will open to allow the sanitizer to be emitted. Door knob assembly may comprise a recoil spring on both the first and second door knob.

Referring to the drawings by numerals of reference there is shown in FIGS. 1-4, various views of sanitizer door knob system 100. Sanitizer door knob system 100 comprises door knob assembly 110 (having first knob 120, second knob 130, and at least one connector shaft 140), sanitizer dispensing assembly 150 (including pull rod 152, gear box 154, at least one spring 158), dispensing tube 160 (having first-end 162, second-end 164, and dispensing-tube-length 166), dispensing-tube-shroud 170, and pump 180, and reservoir 190 which is structured and arranged to be mounted to (or in) door 102. As such, sanitizer door knob system 100 comprises door knob assembly 110; sanitizer dispensing assembly 150, and reservoir 190 in functional combination.

Door knob assembly 110 comprises first knob 120, second knob 130, the at least one connector shaft 140, first knob 120, second knob 130 connected via the at least one connector shaft 140.

Sanitizer dispensing assembly 150 comprises in functional combination pull rod 152, gear box 154, the at least one spring 158, dispensing tube 160, dispensing-tube-shroud 170 and pump 180. Dispensing tube 160 comprises first-end 162, second-end 164, and dispensing-tube-length 166; dispensing-tube-length 166 of dispensing tube 160 defined by first-end 162, second-end 164. Dispensing tube 160 is in fluid communication with reservoir 190, as indicated in FIG. 1.

Reservoir 190 stores fluid comprising sanitizing liquid 192 to be dispensed via pump 180 through second-end 164 of dispensing tube 160; first-end 162 of dispensing tube 160 connected to reservoir 190. Pump 180 is activated via relative turning movement of first knob 120 and second knob 130; gear box 154 being rotationally operated via the at least one connector shaft 140 as moved by turning of first knob 120 and second knob 130. Dispensing tube 160 preferably travels through dispensing-tube-shroud 170; dispensing tube 160 protected via dispensing-tube-shroud 170.

Second-end 164 of dispensing tube 160 preferably comprises nozzle 168 which is adjacent second knob 130 such that sanitizing liquid 192 is able to be atomized by pump 180 and pushed through nozzle 168; sanitizing liquid 192 able to be dispensed onto second knob 130 to prevent transfer of microorganisms. Pump 180 is caused to 'pump' sanitizing liquid 192 as it is pulled into a pumping condition by pull rod 152 via the movement of the gears within gear box 154 (clock-wide/counter-clockwise and thus moving pulley 156)

and returned to a non-pumping condition by the at least one spring 158. Other 'returning means' and activating means for pump 180 may be used. Sanitizer door knob system 100 functions to promote public health by preventing transfer of the microorganisms from off of door knob assembly 110 via dispensing of sanitizing liquid 192 thereon.

Reservoir 190 may be located inside door 102 or outside door 102. Suitable means for mounting, attachment and access will be understood by those skilled in the art of reservoirs. Referring now to pump 180; pump 180 may be manually operated or non-manually operated; wherein pump 180 is able to be activated by a clockwise relative movement of second knob 130 (as turned to open) or by a counter-clockwise relative movement of second knob 130. In this manner pump 180 may be activated to dispense sanitizing liquid 192 regardless of the direction of turning by the individual opening door 102.

In certain embodiments sanitizer door knob system 100 may further comprise slider cap 132 on an exterior of second knob 130 which is structured and arranged to open when second knob 130 is turned to allow sanitizing liquid 192 to be emitted. It should be understood that when second knob 130 is referred to that first knob 120 may alternately comprise the structure to function as described herein 'interchangeably'. Second knob 130 is simply referred to as for example an interior knob such as found on the inside of a washroom where the microorganisms are found in highest concentrations. Sanitizer door knob system 100 may further comprise latch assembly 114, as to functionally provide latching means. The least one connector shaft 140 preferably passes perpendicularly through latch assembly 114.

Gear box 154 comprises a set of meshed gears 155 and preferably pulley 156, as previously mentioned; wherein pull rod 152 is wrapped about pulley 156 such that movement of pulley 156 in a clockwise and counterclockwise direction pulls on pull rod 152 to 'shorten' it's relative length. Pull rod 152 is preferably flexible (cable or the like). Dispensing tube 160 passes through gear box 154.

Door 102 (in so-equipped embodiments) comprises an inlet by which a user can access and fill reservoir 190 located inside door 102. External versions of reservoir 190 are esthetically pleasing such that they 'blend' into the fit and finish of door 102. Reservoir 190 comprises a corrosion-resistant housing.

Sanitizer door knob system 100 may be sold as a kit comprising the following parts: at least one door knob assembly 110; at least one sanitizer dispensing assembly 150; at least one reservoir 190; and at least one set of user instructions. The kit has instructions such that functional relationships are detailed in relation to the structure of the invention (such that the invention can be used, maintained, or the like in a preferred manner). Sanitizer door knob system 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient. Sanitizing liquid 192 may also be included in the kit.

Figure 5:
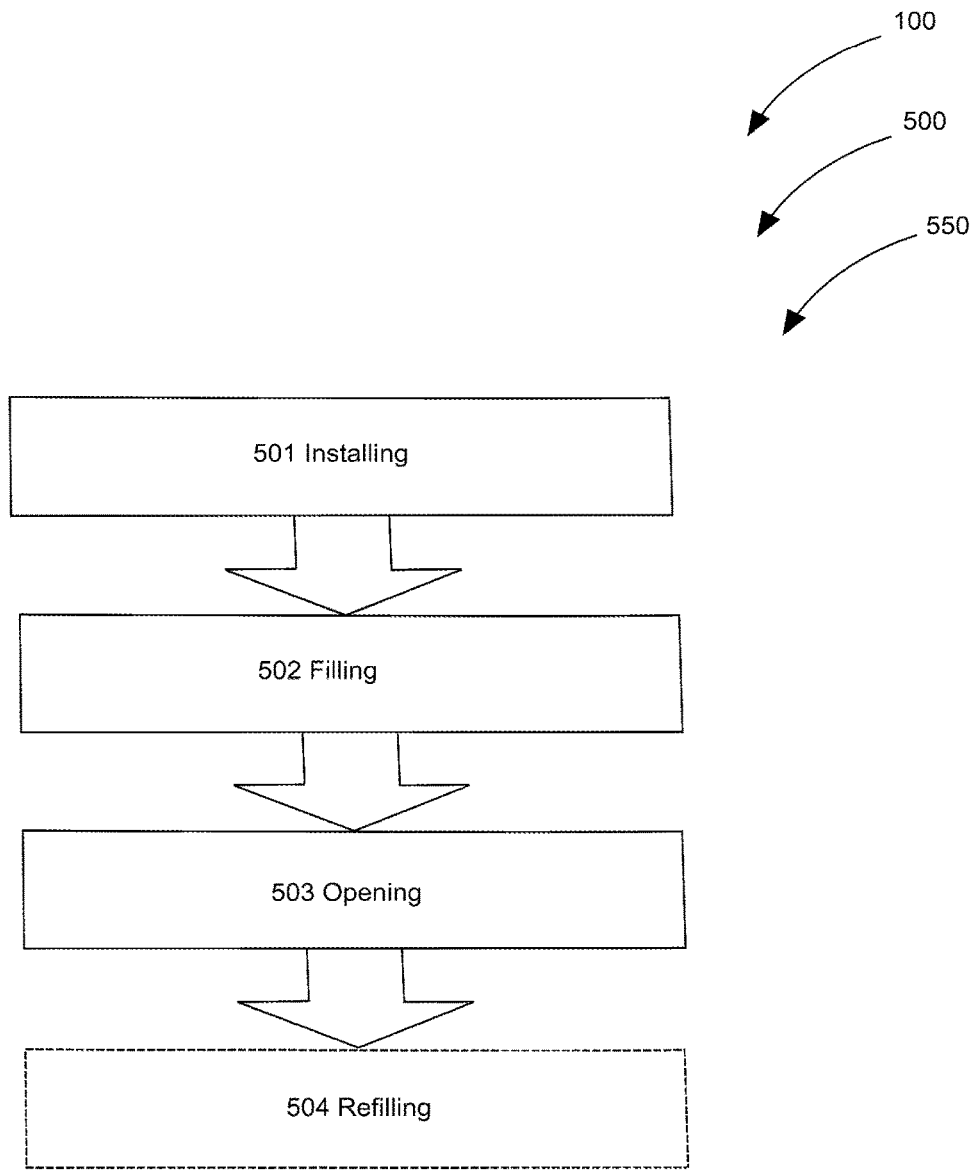
FIG. 5 is a flowchart illustrating a method of use for the sanitizer door knob system according to an embodiment of the present invention of FIGS. 1-4.

Referring now to FIG. 5, a flowchart 550 illustrating a method of use 500 for sanitizer door knob system 100 according to an embodiment of the present invention of FIGS. 1-4.

A method of using (method of use 500) sanitizer door knob system 100 comprises the steps of: step one 501 installing sanitizer door knob system 100, step two 502 filling reservoir 190 with sanitizing liquid 192, and step three 503 opening and closing door 102 (as per normal operation of ingress and egress) via door knob assembly 110 equipped with sanitizer dispensing assembly 150 causing sanitizing liquid 192 to be dispensed onto at least a portion of contacted door knob assembly 110. The method may further comprise the step four 504 of refilling sanitizing liquid 192 into reservoir 190 as necessary.

It should be noted that step 504 is an optional step and may not be implemented in all cases. Optional steps of method 500 are illustrated using dotted lines in FIG. 5 so as to distinguish them from the other steps of method 500.

It should be noted that the steps described in the method of use can be carried out in many different orders according to user preference. The use of "step of" should not be interpreted as "step for", in the claims herein and is not intended to invoke the provisions of 35 U.S.C. § 112, ¶6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A sanitizer door knob system comprising:
   a door knob assembly having;
      a first knob;
      a second knob; and
      at least one connector shaft;
   a sanitizer dispensing assembly including;
      a pull rod;
      a gear box;
      at least one spring;
      a dispensing tube having;
         a first-end;
         a second-end; and
         a dispensing-tube-length;
      a dispensing-tube-shroud; and
      a pump; and
   a reservoir structured and arranged to be mounted to a door;
   wherein said sanitizer door knob system comprises said door knob assembly, said sanitizer dispensing assembly, and said reservoir in functional combination;
   wherein said door knob assembly comprises said first knob, said second knob, said at least one connector shaft, said first knob and said second knob connected via said at least one connector shaft;

wherein said sanitizer dispensing assembly comprises in functional combination said pull rod, said gear box, said at least one spring, said dispensing tube, said dispensing-tube-shroud and said pump;

wherein said dispensing tube comprises said first-end, said second-end, and said dispensing-tube-length, said dispensing-tube-length of said dispensing tube defined by said first-end, and said second-end;

wherein said dispensing tube is in fluid communication with said reservoir;

wherein said reservoir stores fluid comprising sanitizing liquid to be dispensed via said pump through said second-end of said dispensing tube, said first-end of said dispensing tube connected to said reservoir;

wherein said pump is activated via relative turning movement of said first knob and said second knob, said gear box being rotationally operated via said at least one connector shaft as moved by turning of said first knob and said second knob;

wherein said dispensing tube travels through said dispensing-tube-shroud, said dispensing tube protected via said dispensing-tube-shroud;

wherein said second-end of said dispensing tube comprises a nozzle which is adjacent said second knob such that said sanitizing liquid is able to be atomized by said pump and pushed through said nozzle, said sanitizing liquid able to be dispensed onto said second knob to prevent transfer of microorganisms;

wherein said pump is caused to pump said sanitizing liquid as it is pulled into a pumping condition by said pull rod via said movement of said gear box and returned to a non-pumping condition by said at least one spring; and wherein said sanitizer door knob system functions to promote public health by preventing transfer of said microorganisms from off of said door knob assembly via dispensing of said sanitizing liquid thereon.

2. The sanitizer door knob system of claim 1 wherein said reservoir is located inside said door.

3. The sanitizer door knob system of claim 1 wherein said reservoir is located outside said door.

4. The sanitizer door knob system of claim 1 wherein said pump is manually operated.

5. The sanitizer door knob system of claim 1 wherein said pump is non-manually operated.

6. The sanitizer door knob system of claim 1 wherein said pump is activated by a clockwise relative movement of said second knob.

7. The sanitizer door knob system of claim 1 wherein said pump is activated by a counter-clockwise relative movement of said second knob.

8. The sanitizer door knob system of claim 1 further comprising a slider cap on an exterior of said second knob opens when said second knob is turned to allow said sanitizing liquid to be emitted.

9. The sanitizer door knob system of claim 1 further comprising a latch assembly.

10. The sanitizer door knob system of claim 9 wherein said at least one connector shaft passes perpendicularly through said latch assembly.

11. The sanitizer door knob system of claim 1 wherein said gear box comprises a set of meshed gears and a pulley.

12. The sanitizer door knob system of claim 11 wherein said pull rod is wrapped about said pulley such that movement of said pulley in a clockwise and counterclockwise direction pulls on said pull rod.

13. The sanitizer door knob system of claim 1 wherein said dispensing tube passes through said gear box.

14. The sanitizer door knob system of claim 2 wherein said door comprises an inlet by which a user can access and fill said reservoir located inside said door.

15. The sanitizer door knob system of claim 14 wherein said reservoir comprises a corrosion-resistant housing.

16. The sanitizer door knob system of claim 1 wherein said pull rod is flexible.

17. A sanitizer door knob system comprising:
 a door knob assembly having;
  a first knob;
  a second knob;
  at least one connector shaft; and
  a latch assembly;
 a sanitizer dispensing assembly including;
  a pull rod;
  a gear box;
  at least one spring;
  a dispensing tube having;
   a first-end;
   a second-end; and
   a dispensing-tube-length;
  a dispensing-tube-shroud; and
  a pump; and
 a reservoir structured and arranged to be mounted in a door;

wherein said door comprises an inlet by which a user can access and fill said reservoir located inside said door;

wherein said reservoir comprises a corrosion-resistant housing;

wherein said sanitizer door knob system comprises said door knob assembly, said sanitizer dispensing assembly, and said reservoir in functional combination;

wherein said door knob assembly comprises said first knob, said second knob, said at least one connector shaft, and said a latch assembly, said first knob and said second knob connected via said at least one connector shaft;

wherein said at least one connector shaft passes perpendicularly through said latch assembly;

wherein said sanitizer dispensing assembly comprises in functional combination said pull rod, said gear box, said at least one spring, said dispensing tube, said dispensing-tube-shroud and said pump;

wherein said gear box comprises a set of meshed gears and a pulley;

wherein said pull rod is wrapped about said pulley such that movement of said pulley in a clockwise and counterclockwise direction pulls on said pull rod;

wherein said pull rod is a flexible cable;

wherein said dispensing tube comprises said first-end, said second-end, and said dispensing-tube-length, said dispensing-tube-length of said dispensing tube defined by said first-end, and said second-end;

wherein said dispensing tube is in fluid communication with said reservoir;

wherein said reservoir stores fluid comprising sanitizing liquid to be dispensed via said pump through said second-end of said dispensing tube, said first-end of said dispensing tube connected to said reservoir;

wherein said pump is activated via relative turning movement of said first knob and said second knob, said gear box being rotationally operated via said at least one connector shaft as moved by turning of said first knob and said second knob;

wherein said dispensing tube travels through said dispensing-tube-shroud, said dispensing tube protected via said dispensing-tube-shroud;

wherein said second-end of said dispensing tube comprises a nozzle which is adjacent said second knob such that said sanitizing liquid is able to be atomized by said pump and pushed through said nozzle, said sanitizing liquid able to be dispensed onto said second knob to prevent transfer of microorganisms;

wherein said pump is caused to pump said sanitizing liquid as it is pulled into a pumping condition by said pull rod via said movement of said gear box and returned to a non-pumping condition by said at least one spring;

wherein said pump is manually operated;

wherein said pump is activated by a clockwise relative movement and alternately a counter-clockwise relative movement of said second knob; and wherein said sanitizer door knob system functions to promote public health by preventing transfer of said microorganisms from off of said door knob assembly via dispensing of said sanitizing liquid thereon.

18. A kit comprising:
said sanitizer door knob system of claim 17 and
a set of user instructions.

19. A method of using a sanitizer door knob system comprising the steps of:
installing said sanitizer door knob system of claim 1;
filling said reservoir with sanitizing liquid; and
opening and closing said door via said door knob assembly equipped with said sanitizer dispensing assembly causing said sanitizing liquid to be dispensed onto at least a portion of said door knob assembly contacted by a user.

20. The method of claim 19 further comprising the step of refilling said sanitizing liquid into said reservoir as necessary.

* * * * *